United States Patent

Ruottu et al.

[11] Patent Number: 6,045,688
[45] Date of Patent: Apr. 4, 2000

[54] METHOD BASED ON A FLUIDIZED-BED REACTOR FOR CONVERTING HYDROCARBONS

[75] Inventors: Seppo Ruottu, Karhula; Kari Kääriäinen, Vantaa; Jyrki Hiltunen, Sipoo, all of Finland

[73] Assignee: Neste OY, Espoo, Finland

[21] Appl. No.: 08/921,384

[22] Filed: Aug. 29, 1997

[30] Foreign Application Priority Data

Aug. 30, 1996 [FI] Finland .................................. 963404

[51] Int. Cl.[7] ............................. C10G 11/18; C10G 9/32; C07C 5/333; C07C 2/00
[52] U.S. Cl. ......................... 208/113; 208/153; 208/157; 208/161; 208/126; 208/127; 585/654; 585/700; 585/924; 423/651
[58] Field of Search ................................. 208/153, 155, 208/157, 161, 113, 126, 127; 585/654, 700, 924; 423/651

[56] References Cited

U.S. PATENT DOCUMENTS

| | | | |
|---|---|---|---|
| 2,358,497 | 9/1944 | Egloff | 196/52 |
| 2,448,135 | 8/1948 | Becker et al. | 208/148 |
| 2,514,288 | 7/1950 | Nicholson | 196/52 |
| 2,515,155 | 7/1950 | Munday | 55/343 |
| 2,525,925 | 10/1950 | Marshall | 196/52 |
| 2,671,796 | 3/1954 | Garbo | 518/728 |
| 4,152,393 | 5/1979 | Callahan et al. | 422/144 |
| 4,957,617 | 9/1990 | Owen et al. | |

FOREIGN PATENT DOCUMENTS 2240285  7/1991  United Kingdom.

*Primary Examiner*—Walter D. Griffin
*Attorney, Agent, or Firm*—Birch, Stewart, Kolasch & Birch, LLP

[57] ABSTRACT

The invention relates ro a method of converting hydrocarbons. According to the method, a gaseous or liquid hydrocarbon feed is passed into a circulating fluidized-bed reactor, wherein the feed is converted at a high temperatue under the influence of particulate matter kept in a fluidized state, and the converted hydrocarbon products are removed from the reactor in a gaseous phase. According to the invention, a circulating fluidized-bed reactor (1–3; 41–43) is used having an axially annular cross section and being equipped with a multiport cyclone (14,17; 52,63) for the separation of the particulate matter from the gas-phase reaction products. The reaction space comprises an intershell riser space (13; 50) formed between two concentrically located cylindrical and/or conical envelope surfaces. The separation of particulate matter from the gas-phase reaction products is performed by means of a multiport cyclone equipped with louvered vanes (14; 63).

12 Claims, 2 Drawing Sheets

METHOD BASED ON A FLUIDIZED-BED REACTOR FOR CONVERTING HYDROCARBONS

FIELD OF THE INVENTION

The invention relates to a method according to the preamble of claim 1 for converting hydrocarbons.

According to the present method, a gaseous or liquid hydrocarbon feed to be processed is admitted into a reactor operated with a circulating mass of solids kept in a fluidized state (later called a "fluidized-bed reactor"), where it undergoes conversion at an elevated temperature in the presence of a fluidized solids medium capable of stabilizing the energy balance of the conversion process.

The invention also concerns an apparatus according to the preamble of claim 11 for processing and convey hydrocarbons.

BACKGROUND OF THE INVENTION

Generally, fluidized-bed reactors are used in the conversion processes of hydrocarbons. Herein, a catalyst or similar particulates suited for heat exchange and fluidization is kept in a fluidized state by the upward flow of a gaseous hydrocarbon. Typically, the minimum fluidization flow is provided by means of a prefluidizing gas such as steam or recirculation of the product gas. In conventional fluidized-bed reactors operated with the linear flow rate of the medium adjusted close to the minimum fluidization flow rate, the particulate matter remains in the fluidized bed of the reactor, instead of becoming carried over from the reactor in significant amounts along with the hydrocarbon flow.

By contrast, at flow rates appreciably higher than the minimum fluidization flow rate, the upper surface of the fluidized bed becomes less defined, in fact, forming a zone in which the soids content deeses along the vertical axis. At sufficiently high flow rates this effect leads to a situation in which practically all the particulate matter will be carried over along with the hydrocarbon flow maintaining the fluidized state. Then, the solids must be separated from the hydrocarbon outlet flow leaving the reactor by means of cyclones and are recirculated either directly or via a regenerator back to the bottom section of the reactor. Such a system is called either a circulating fluidized bed (CFB), or analogously, a circulating fluidized bed reactor (CFBR), if a chemical reaction occurs in the suspended solids.

PRIOR ART

One of the most generally used reactor systems in the art for catalytic cracking of hydrocarbons is the fluid catalytic cracking (FCC) equipment comprising chiefly a riser tube (reactor) operated in the fast fluidization flow state, cyclone separators of the catalyst from the reaction product that are operated in a diluted suspension phase and a large-volume regenerator operated in the fluidized-bed state. An example of such FCC equipment is represented by the embodiment illustrated in U.S. Pat. No. 4,957,617.

Other applications utilizing catalytic fluidized-bed or FCC reactors are, e.g.,:

catalytic reforming,
preparation of phthalic acid anhydride or maleic acid anhydride,
oxidative dimerization of methane,
Fischer-Tropsch synthesis,
dehydrogenation,
chlorination and bromination of methane, ethane and similar alkanes, and
conversion of methanol into olefins or gasoline.

Noncatalytic processes using fluidized-bed reactors are, e.g.,:

thermal cracking,
catalyst regeneration, and
gasification processes.

Suitable physical processes are, e.g.,:

drying,
beat exchange between two gases, and
adsorption.

Of the above-listed processes, significant economical values pertain particularly to catalytic cracking, dehydrogenation, the Fischer-Tropsch synthesis, methanol conversion process to olefins (MTO) and possibly the process for oxidative dimerization of methane which still is at an experimental stage.

Conventional reaction environments have certain essential drawbacks. For instance, the reaction time of a conventional fluidized-bed reactor is difficult to control, and the erosion of the catalyst/solids and reactor structures is a major equipment complication. These problems are accentuated particularly when the process control presumes a short residence time combined with a high process temperature. In chemical reactors based on a scaled design, the residence times of both the gas and the solids must remam unchanged. However, with a larger reactor diameter, the residence time of solids in the reactor tends to become longer, because the reflux of the solids close to the walls increases. To counter this effect, the flow rate must be increased, which further requires a higher reactor to keep the gas residence time unchanged.

Apparatuses for separation of gas from solids/catalyst particulates that forms an essential part of process equipment are also hampered by problems discussed in detail below:

Particulate matter and product gas leaving the reactor are separated from each other in cyclone separators utilizing centrifugal force. GeneraUy, cyclones have a single-port structure, i.e., they have only one inlet nozzle for tee particulate matter suspension. In practice, the maximum diameter of single-port cyclones is about 1 m, whereby due to flow capacity requirements a plurality of cyclones must be connected in parallel, and further, two or three in series in the direction of the gas flow.

A cyclone is rated effective if it can separate small particles of less than 15 μm diameter from the gas flow. Conventionally, cyclone separators have either a coiled or spiralled structure. The particulate matter suspension is directed as a tangential flow into the cylindrical section of the cyclone, whereby the solids are separated under the centrifugal force as the flow circulates in the cyclone typically 7–9 revolutions within the cylindrical section and the conical section forming a continuation thereof. Also axial cyclones are known in which the gas flowing through a tube is forced into a circulating motion by means of vanes, whereby the solids under the centrifugal force are driven against the tube wall and separated thereon from the gas flow. The most common cyclone type is the so-called Zenz cyclone, in which the proportions of the different parts of the cyclone are standardized permitting the design of the cyclone to be based on graphs and computational formulas. The separation efficiency of the cyclone is enhanced by a large number of flow revolutions in the cyclone chamber, high flow rate at the inlet nozzle, high density of solids, small cross section of the inlet nozzle port and low viscosity of the gas.

In conventional single-port cyclones, the solids flow impinges on the cyclone inner wall as a homogeneous gas-suspended jet of high flow velocity which in primary cyclones is typically in the range 20–25 m/s, in secondary cyclones about 35 m/s, and in tertiary cyclones about 40 m/s. The flow rate of the impinging jet must be high, because the cyclone inlet nozzle width (jet width) is generally, e.g., in standardized Zenz cyclones about one-fourth of the cyclone diameter, and the particulate matter must be brought over the entire width of the impinging jet close to the cyclone inner wall in order to achieve separation of the solids. In this type of cyclones, the point most susceptible to erosion is the area of the cyclone inner wall receiving the impact of the suspended solids jet.

SUMMARY OF THE INVENTION

It is an object of the present invention to overcome the drawbacks of the above-described prior-art technology and to implement fluidization in a novel type of fluidized-bed reactor offering maximized efficiency of lateral mixing. It is a further object of the invention to provide a reactor structure in which the solids after the reaction are separated with a maximum speed and efficiency from the product gases.

According to the invention, the conversion of hydrocarbons is performed in a circulating fluidized-bed reactor in which the reaction space, i.e., the fluidization space of the reactor comprises an inrshell space of axially annular cross section remaining between two concentrically located cylinders or cones, in which space the feed, typically in the liquid phase, is first vaporized and subsequently converted into reaction products at an elevated temperature in the presence of particulate matter, which may additionally have catalytic properties. The feed may alternatively be in a gaseous phase. After leaving the reactor, the reaction product is generally distilled or purified by other methods into usable fractions. The novel reactor is suitable for, i.a., catalytic and thermal cracking, dehydrogenation and oxidizing dimerization of metane.

Further according to the invention, the particulate matter is separated from the reaction gas by means of a multi-inlet (in the following also "multiport") cyclone, which is located directly above the axially annular reactor riser space. This arrangement makes it possible to shorten the residence time of the reaction, because a multiport cyclone offers faster and more efficient separation of particulate matter from the reaction gas flow over a single-port cyclone. From the cyclone, the particulate matter can be recirculated to a regenerator via a solids return channel, or the downward return leg, which is formed by an intershell space of axially annular cross section remaining between two concentrically located cylinders or cones.

More specifically, the method according to the invention is a method of converting hydrocarbons comprising: step a) passing a gaseous or liquid feed into a circulating fluid bed (CFB) reactor having a reaction space wherein particulate matter is in the fluidized state; step b) converting the feed at a temperature of 100 to 1300° C.; and step c) removing the converted hydrocarbon products wherein said circulating fluidized bed reactor has an axially annular cross-section and is equipped with a multi-inlet cyclone disposed along an upper end, and inside, of the reactor for the separation of the particulate matter from the converted hydrocarbon products.

Furthermore the apparatus according to the invention is as described hereinabove for practicing the method according to the invention.

In the description of the present invention, the term "residence time" refers to the mean residence tme of hydrocarbon molecules from the infeed point of the reactor to the cyclone outlet tube, said time varying in the range 0.05–10 s, typically 0.1–5 s, and the term "elevated temperature" refers to a temperature range of 100–1000° C. The reactor is suited for the following processes and others: catalytic and thermal cracking, dehydrogenation, Fischer-Tropsch synthesis, preparation of maleic acid anhydride and oxidative dimerization of methane.

The term "reaction product" is used to refer to products resulting from the above-mentioned processes. Accordingly, the reaction products may contain, e.g., cracking and dehydrogenation products chiefly comprising light olefins such as propene, n-butenes, isobutene and amylenes.

The term "solids" is used to refer to the particulate matter which forms a suspension in the reaction space. The particulate matter typically comprises solid catalyst particles if the reactor is used for catalytic reactions. When the reactor is used for thermal processes, the particulate matter is formed by inert particles serving to transfer heat or material into the reaction space or away terefrom. The catalyst is selected to suit the process. Accordingly, catalytic cracking typically uses natural or synthetic aluminum silicates zeolites and alumina. Conventional zeolites include zeolites X and Y which can be stabilized by lanthanides. Dehydrogenation processes use chromium-aluminum oxide catalysts, for instance.

Generally, the invention is most appropriately applied to high-temperature endo- and exothermic processes requiring a short residence time such as catalytic or thermal cracking, dehydrogenation, Fischer-Tropsch synthesis, MTO and oxidative dimerization of methane. According to a first preferred embodiment, the reactor according to the invention is used for catalytic cracking, wherein the reactor feed may be light gas oil, heavy gas oil or light bottom oil in order to produce light olefins and/or gasoline. In cracking, the process temperature is about 520–650° C. and the residence time in the range 0.5–5 s.

According to a second preferred embodiment, the reactor according to the invention is used for thermal cracking, wherein bottom oil or other heavy hydrocarbon is fed into the reactor for cracking into lighter hydrocarbon fractions. The process temperature is 650–1000° C. and the residence time in the range 0.2–0.5 s.

According to a third preferred embodiment, the reactor is used in the dehydrogenization of a feed comprising pentanes, isobutane, n-bumane, propane or a mixture thereof at a process temperature of 650–750° C. and a residence time in the range 0.4–2 s in order to prepare amylenes, isobutene, n-butenes, propene or mixtures thereof.

According to a fourth preferred embodiment, the reactor is used for oxidative dimerization of methane in natural gas feed at a process temperature of 800–900° C. and a residence rime in the range 0.08–0.3 s.

According to a fifth preferred embodiment, the reactor feed comprising hydrocarbons is gasified, that is, partially oxidized, with air or other oxygen-containing gas into synthesis gas, that is, gas contining at least carbon monoxide and hydrogen. Partial thermal oxidization occurs at 1000–1300° C. and partial catalytic oxidization at 700–1000° C. with a residence time essentially sufficient to achieve a chemical reaction equilibrium. In order to increase the proportion of hydrogen in the produced synthesis gas and to achieve thermal equilibrium, steam may additionally be introduced into the reaction.

Next, the invention will be examined closer with the help of a detailed description and a few exemplifying emibodiments, whose equipment constructions are elucidated by making reference to appended drawings.

DETAILED DESCRIPTION OF THE INVENTION

Figure 1:
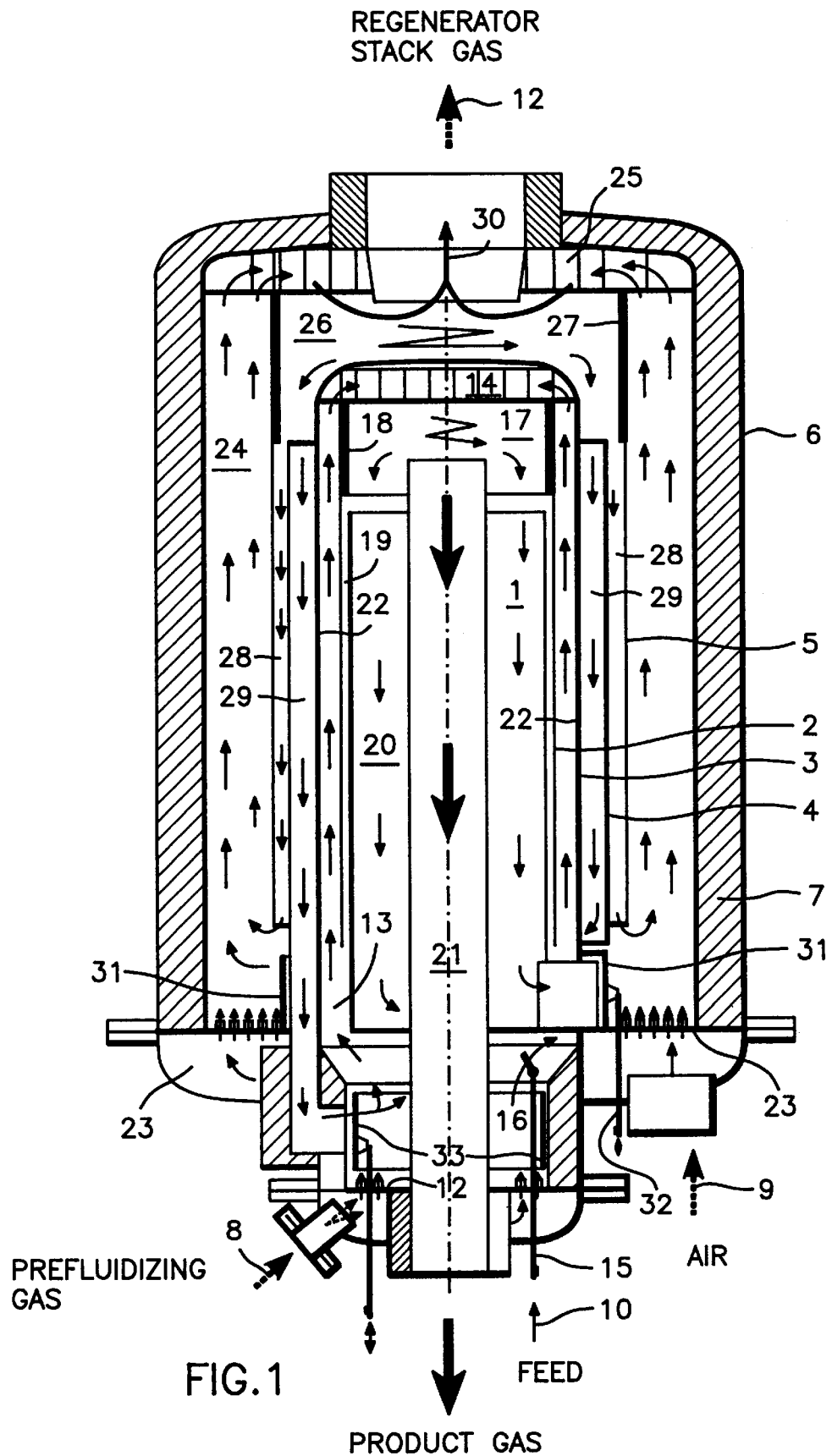
FIG. 1 is a side view of a preferred embodiment of the structure of an apparatus paticularly well suited for use in catalytic cracking and heat exchange processes.

A reactor according to the invention suited for conversion of hydrocarbons, generally from a feed of paraffinic hydrocarbons in a circulating bed reactor, principally comprises a reaction space formed between two concentrically located upright cylinders or cones, whereby the reaction space and the downward return leg has an axially annular cross section. The infeed nozzles, through which the liquid or, in certain cases, gaseous feed is passed into the reaction space, are located in the bottom section of the reaction space. The feed nozzles are normally aligned upward. The inert solids or catalyst is taken along a downward return leg, which in an axially annular fashion surrounds the reactor, to the bottom section of the reactor via an annular port provided in the outer shell of the reactor, or alternatively, via a number of smaller openings made to said reactor outer shell. The solids flow rate into the reactor can be advantageously controlled by means of a cylinder adapted about the reactor outer shell, whereby the rotation or elevation of said cylinder allows throttling of the solids inlet port. Conventional valves may also be used for controlling the solids flow from the downward return leg back to the reactor.

In such a preferred embodiment of the invention in which a reactor according to the invention is used for catalytic cracking, the reactor may be adapted concentric with another reactor. Then, the inner reactor of the two is used as a cracking reactor, while the outer serves as a regenerator in which the catalyst is regenerated and heated to a desired temperature. From the reactor proper, the catalyst is raferred to te regenerator via the axially annular outlet channel, or downward return leg, and channels made to the fluidization space of the reactor. The downward return leg, also known as the catalyst return channel to the reactor, forms a space of axially annular cross section.

The solids flow into the reaction space via the solids inlet port and will be mixed in the axially annullar riser of the reactor with the upward prefluidizing gas flow in which the solids pass in the axially annular riser to the level of the feed inlet nozzles. Here, the liquid feed, which is atomized into small droplets, is vaporized and heated to the reaction temperature as it meets the hot upward flow of the particulate matter. Due to the feed vaporization, the solids flow velocity will increase. As the flow velocity is substantially higher than the minimum fluidization velocity, the solids will follow the gas flow, however, at a velocity slightly lower than the gas flow velocity. A separating unit formed by a multiport cyclone of the reactor, which is placed to the upper end of the reaction space, performs separation of particulates from the solids suspension. From the cyclone, the solids are passed after regeneration back to the reactor via the axially annular downward return leg surrounding the reactor riser. The reaction product gases are removed via the central tube of the cyclone.

The riser channel with the axially annular cross section can be formed between, e.g., two concentric cylindrical surfaces of revolution, whereby the inner surface of the outer cylindrical shell forms the outer wall of the reaction space and the outer surface of the inner cylindrical shell forms the inner wall of the reaction space. Hence, a reactor construction according to the invention formed from two concentrically erected cylindrical shells results in a compact, sturdy and easy-to-install reactor structure.

In the vertical direction, the axially annular cross section of the reactor riser space can be made constant, whereby the spacing of the reactor walls formed by upright cylindrical or conical shells is unchanged throughout the height of the reactor riser. Alternatively, the reactor cross section can be made variable as a function of die height coordinate, which option can be utilized to affect the fluidization characteristics of the reactor.

When desired, the reactor riser space may be divided axially into concentric segments. Such segmental division can be implemented by installing additional concentric cylindrical or spiralling baffles in the reaction space formed between the two concentric cylndrical shells. The use of spiralling baffles combined with a reduced pitch angle of the spiralled baffle plates gives an option of increasing te residence tuie of hydrocarbons and the catalyst in the riser channel at a given level of the reactor. In certain cases, the baffles may be necessary as stiffeners of the reactor structure. Alternatively, the same result is obtained by constructing the reactor riser space from a plurality (e.g., 6–20) of axially aligned parallel tbes which are arranged equidistantly spaced in a circular fashion.

As is evident from the discussion above, the term "axially annular cross section" used in the context of the present invention must be understood to include all the possible embodiments in which the elements that form the cross section of the reactor riser to be arranged at least essentially along the perimeter of an axially annular reactor riser. The reactor axial cross section need not necessarily have the shape of a continuous circle, while this embodiment is considered advantageous. More precisely: an axially annular reactor riser comprises a space of axially annular cross section which may be contiguous or divided by, e.g., baffle plates or tubes into axially parallel, upward running riser segments.

To the upper section of the reactor riser is connected a multiport cyclone serving as the solids separating unit which removes particulate matter from the reaction product flow. In such a cyclone, the solids suspension to be processed is admitted via a plurality of inlet ports into the cyclone chamber. The inlet ports may be symmetrically or asymmetrically spaced from each other along a circle about the vertical axis. Advantageously, the ports are arranged in a symmetrical fashion, since the reactor riser channel has an axially annular cross section, which means that the flow pattern over the cross section of the riser channel is uniform. Herein, the cyclone is provided with vanes which generate the vortex required for centrifugal separation. Generally, the vanes are arranged in a circular fashion about the perimeter of the cyclone chamber so as to form a louver which provides a number of parallel gas inlet ports.

The invention offers significant benefits. Accordingly, the multiport cyclone adapted above the axially onnllar reactor riser gives essential advantages in flow dynamics and process engineering over conventional arrangements and generally used single-port cyclones. Now, the cyclone can be constructed in a similar fashion as a conventional multiport cyclone, however, most advantageously using an annular louvered inlet, whereby a maximum portion of the annular inlet port area is available for admitting the gas-suspended solids flow. Later in the text will be elucidated the principal benefits of the construction according to the invention that are provided by both the riser with the axially annular cross section and the multiport cyclone connected thereto.

As noted above, the lateral mixing of solids in the apparatus according to the invention occurs over a shorter distance han in a conventional tubular riser. Resultingly, temperature and concentration differences are equalized rapidly and in a more homogenous fashion than in tubular reactors, which is an important design target in chemical fluidized-bed reactors. As an example, it may be noted herein that in a full-scale axially annular riser with an outer diameter of about 1.67 m and an inner diameter of about 1.35 m, whereby the lateral mixing distance is 160 mm. By contrast, a tube riser of the same cross-sectional area (0.76 $m^2$) has a tube inner diameter (lateral mixing distance) of 983 mm, which is six-fold. Here, if a smaller lateral mixing distance of the tube reactor is desirable, the reactor height must be increased substantially.

Owing to the small lateral mixing distance, the feed flow over the cross-section of the reactor can be made uniform. Also the prefluidization zone, in which the flow is stabilized prior to the feed point, can be made shallower due to the above-described reason.

It can be father noted that the axially annular riser according to the invention operates at a smaller flow velocity than a tubular riser, which reduces the erosion of structural materials in the reactor and makes scaling of equipment size easier and more successful. In addition, the equipment may be implemented with a lower height, whereby problems associated with structural design and thermal expansion are alleviated.

According to a preferred embodiment, the apparatus according to the invention may comprise an inner reactor having a riser space of axially annular cross section formed between two concentric cylindrical shells and a surrounding outer regenerator in which the contaminated catalytic solids or cooled heat transfer particulates can be regenerated for return to the process. Obviously, the reaction space concept according to the invention may be applied to varied processes and also combined with regenerator constructions different from that described above. However, the regenerator embodiment discussed herein is particularly advantageous as the distances of solids lateral travel are shortened significantdy and even a large regenerator can be implemented with a short height in regard to its diameter, whereby a smaller footprint is required, the thermal expansion problems of the regenerator are reduced essentially and the reactor-regenerator construction forms a compact, stiff and easy-to-install entity.

The construction according to the invention overcomes erosion problems by flow design methods: in a multiport cyclone the solids suspension flow is incident on the cyclone irnner surface as a number of small solids jets instead of entering as a single high-impact solids flow, whereby erosion of structures is smaller and smoother. A cyclone connected to a reactor according to the invention may have its height reduced to half the volume of a standard cyclone (resulting in halved residence time), because the novel cyclone due to its improved flow dynamics can be dimensioned shallower (owing to the narrow inlet ports).

Due to the multiport construction, the cyclone inlet ports can be made narrow, whereby the catalyst layer becomes shallow, and the flow velocity at the inlet port may be essentially smaller than in conventional single-port cyclones in which reduction of the inlet port width would require an increased channel height, resulting in a higher cyclone and making the communicating channel longer and clumsy in shape. The possibility of using a reduced cyclone inlet flow velocity contributes to a further lowered erosion rate, which is dependent on the flow velocity by a power of 4 to 5.

In an FCC preseparation cyclone, tests have shown the gas residence time to be in the order of 1.0–2.0 s, from the riser top to the cyclone outlet, after which the reaction product will further stay in the separation vessel at an elevated temperature for 5–40 s. During this time, valuable compounds will be lost as a consequence of chemical reactions. By contrast, the construction according to the present invention offers an exactly controllable reaction time as the catalyst caters the cyclone simultaneously from each point of the riser top. When required, the product can be cooled immediately at the exit point of the cyclone outlet nozzle and no separation vessel is needed.

The fact that a multiport cyclone achieves a vastly improved separation efficiency over a conventional cyclone is also evident from the following example:

EXAMPLE I

In tests carried out at room temperature, a cyclone of 465 mm diameter with full-area inlet ports and straight vanes, the separation efficiency was 99.99% at 5.6 m/s inlet flow velocity when the cross-sectional mass flow rate of the catalyst was over 200 $kg/m^2s$. In a conventional Zenz cyclone with compatible dimensions and flow rates, the separation efficiency was 99.10% computed by particle size fractions. A comparison of these separation efficiencies makes it clear that the novel cyclone with multiple narrow inlet ports according to the invention offers a superior efficiency when the design goal is to avoid high flow velocities leading to erosion.

Details of the structures used in the apparatuses according to the invention will be evident from the appended drawings. In the following detailed description, the circulating solids are denoted by abbreviation "CS" and the example process is catalytic cracking using a liquid hydrocarbon as the feed.

Referring to FIG. 1, a preferred embodiment of the apparatus according to the invention comprises two concentrically adapted cylindrical CS reactors separated by an intermediate shell 22, of which the inner will later be called the "reactor" and The outer the "regenerator".

The reactor unit is made from three concentrically mounted, essentially cylindrical tubes 1, 2 and 3, whose intertube spaces form spaces 20, 19 and 13 of axially annular cross section. Among these, the desired reaction is carried out in the space 13. The tubes which are made from steel, for example, are mounted with their longitudinal axes aligned concentrically vertical. Above the axially annular riser space 13, as a continuation of tubes 2 and 3, is mounted a multiport cyclone 14, 17 having louvered vanes 14 fixed to its outer wall. The cyclone is provided with a center tube 21 for removal of the product gas, while transfer channels 19 and 20 are provided in the inner space of the inner steel tube 3 for removal of the solids separated from the gaseous phase in the cyclone.

Inside the reactor outer shell 3, the regenerator unit comprises three concentrically mounted, essentially cylindrical tubes 4, 5 and 6, made from steel, for example, whose intertube spaces form spares 29, 28 and 24 of axially annular cross section. Among these, catalyst regeneration is carried out in the space 24. From inside, the pressure shell 6 is lined with an insulating material layer 7 in order to maintain the shell temperature at a reasonable level for shell strength. In a similar fashion as in the reactor, above the axially annular space 24 is mounted a multiport cyclone 25, 26. whose vanes are fixed either to the cylinrical pipe 5 or the pressure shell 6. The cyclone is provided with a center tube 30 for removal of the stack gas formed in the regenerator, while transfer channels 28 and 29 are provided by means of steel tubes 5 and 6 for removal of the solids separated from the gaseous phase in the cyclone.

The fluidization gas flow of the reactor is denoted in the diagram by reference numeral 8. The gas flow 8 enters the reaction space through a fluidization bottom 12 above which it is first mixed with the solids entering via a return channel 20 via a valve 31, and Then higher in the reactor riser, with the feed flow 10 injected via spray nozzles 17 of feed pipes 16, whereby the feed is instantaneously vaporized under contact with the hot solids flow. The mixed gas flows 8 and 10 move in a gaseous phase along the axially annular riser 13 simultaneously carrying the entrained solids therewith into the vanes 14 of the reactor cyclone. The solids release heat into a reaction or other process occurring in the riser 13 and to the vaporization of the feed flow 10, whereby the temperature of the solids falls. From the vanes 14, the gas and entrained solids enter tangentially the interior of the inner reactor cyclone chamber 17, where the particulate matter is separated by impinging on the cyclone inner wall 18 and falling into the solids transfer channels 19 and 20. When required, a portion of the solids can be reframed as an overflow back to the reactor bottom section via an axially annular channel 19. While the channel 19 is not essential to the function of the apparatus, it may in some cases be advantageous to the operation of the reaction. In the channel 20, the solids dribble downward in a dense phase, whereby the mixing of the gas flows between the reactor and the regenerator via the solids transfer channel 20 will be inhibited. The gas flow 11 entering the reactor cyclone exits the reactor via the center tube 21 of the inner cyclone. The solids flow from the reactor into the regenerator is controlled by means of a valve 31 equipped with a cylindrical control element, which is arranged mechanically movable by means of bars 32.

The regenerator is adapted about the reactor so that these units are separated from each other by a transfer channel 29 filled with solids in a dense phase. In a similar fashion with the reactor, the regenerator is located in the intershell space remaining between two cylindrical envelope surfaces formed by the apparatus shell and the reactor tube mounted inside the shell. Between said reactor cube and said outer cylindrical shell structure of the reactor is further mounted a cylindrical wall to provide said solids transfer channel 29. An oxygen-containing gas flow 9 enters the regenerator via a fluidizing distributor 23 and rises in the axially annular riser channel 24 simultaneously therewith carrying the solids into the vanes 25 of the regenerator cyclone. In the regenerator, coke possibly accumulated on the surface of the solids and organic compounds penetrated in the pores thereof are oxidized, that is, burned in the riser channel 24, whereby the solids temperature is elevated.

The regenerator cyclone chamber 26 is located above the reactor proper. In the cyclone chamber 26, the solids are separated by impinging on the cyclone wall 27 and subsequently fall into channels 28 and 29. The return channel 29 passes the solids back to the reactor. That excess portion of the solids which fails to enter the return channel will fall back to the regenerator bottom section as an overflow via the channel 28. The catalyst or similar particulate matter is advantageously kept in a fluidized state during its passage in the internal return channel, whereby a control valve is redundant. The stack gas 12 of the regenerator is removed via the central tube 30 of the regenerator cyclone. The solids dribbling slowly downward in the return channel 29 in a dense phase prevent communication between the gas spaces of the reactor and the regenerator. The solids flow rate from the regenerator to the reactor is controlled by moving the cylindrical control element of a valve 33 mechanically via bars 34 connected thereto.

Figure 2:
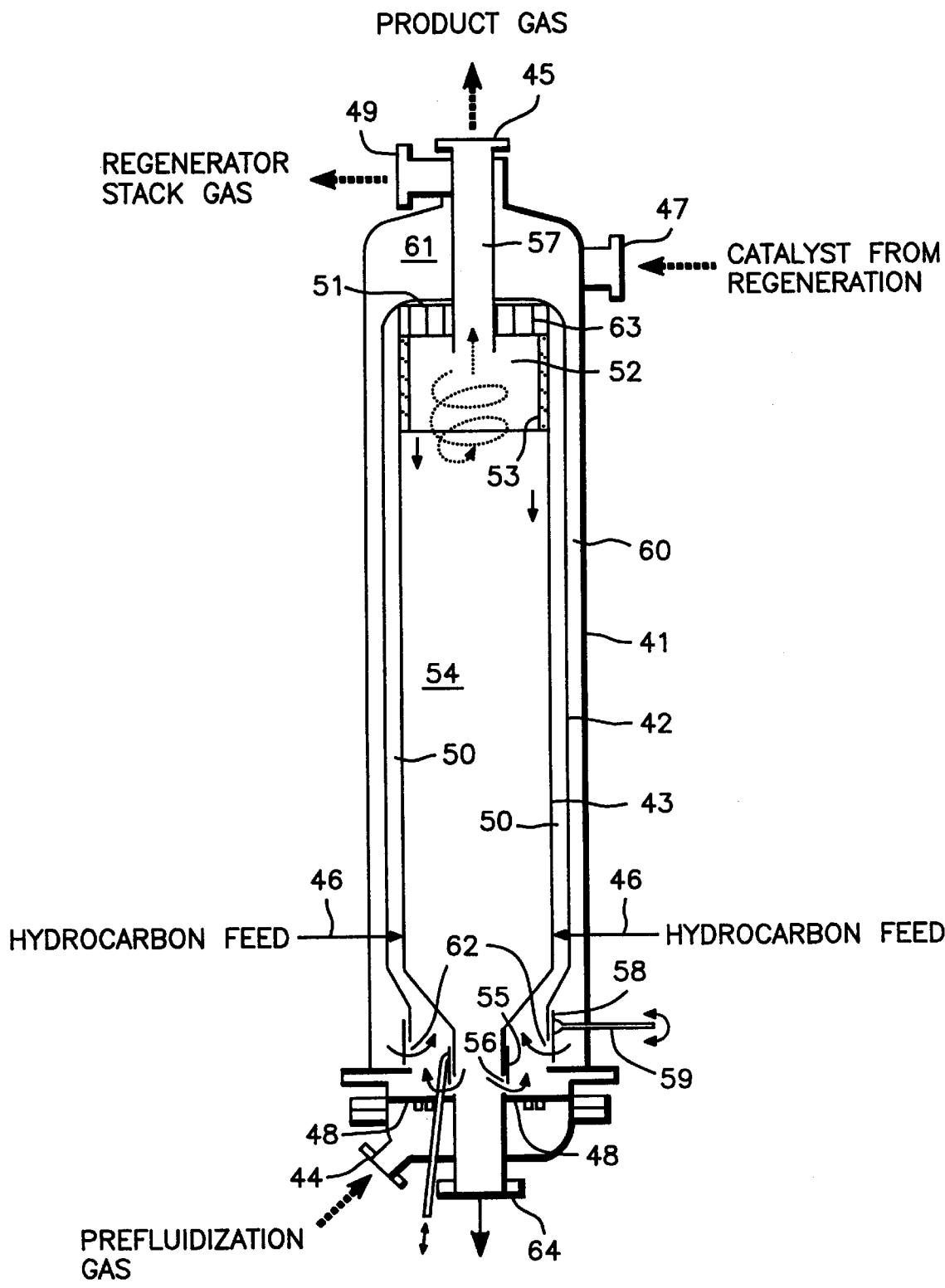
FIG. 2 is a side view of the basic structure of a simplified reactor embodiment according to the invention.

Now referring to FIG. 2, the apparatus shown therein comprises an elongated reactor 41 having its longitudinal axis aligned essentially vertical. The innermost section of the reactor comprises two concentrically mounted, essentially cylindrical tubes 42 and 43, whose intertube space forms a space 50 of axially annular cross section that serves as the riser of the reactor. Above the axially annular space, as an extension of the tubes 42 and 43, is mounted a multiport cyclone 52, whose louvered vanes 63 are fixed to the outer wall thereof. The cyclone is provided with a center tube 57 for removal of the product gas, while an inner tube 43 acts as an intermediate storage silo for the contaminated catalyst separated from the gaseous phase in the cyclone and as a solids transfer channel 54. Between the outer tube 42 and the reactor shell 41 is formed a return channel 60 of axially annular cross section for the return of the regenerated catalyst. To the bottom section of the reactor outer shell 41 is connected a prefluidizing gas inlet nozzle 44 communicating with the reactor riser 50, a product gas discharge nozzle 45 connected to the cyclone center tube 57, liquid hydrocarbon infeed nozzles 46, a catalytic solids infeed nozzle 47 connected to the return channel of regenerated catalyst, and a regeneration stack gas discharge nozzle 49 through which the gas carried over from the regenerator with the regenerated catalyst is removed. To Me upper section of the return channel 60 may further be connected a catalyst return chamber 61 that can be a cyclone, for instance, in which the regenerated catalyst is separated from the gas carried over with the catalyst and is redistributed uniformly into the return channel. From the transfer channel 54, the contaminated catalyst is passed via a discharge nozzle 64 into the regenerator.

An example of how the above described reactor is used for cracking is described in the following manner:

EXAMPLE II

The fluidization gas is passed via the nozzle 44 and the fluidizing distributor bottom 48 into the reactor riser 50 of axially annular cross section, wherein thereto is mixed first the regenerated catalyst from the return channel 60 via an opening 62 and subsequently the hydrocarbon feed 46 injected via spray nozzles. The liquid hydrocarbon feed will be vaporized instantly under contact with tie hot catalyst. The catalyst releases its heat in the riser 50 into the vaporization of the liquid hydrocarbon feed and the cracking reaction, whereby its temperature falls. The mixed gas flows pass in a gaseous phase upward along the axially annular riser 50, thereby carrying the catalyst into the vanes of the reactor cyclone. From the vanes 51, the gas and the entrained catalyst particles pass tangentially into the reactor cyclone chamber 52, wherein the catalyst particles are separated by impinging on the cyclone chamber wall 53 and then fall into the contaminated catalyst collecting silo and the transfer channel 54. The contaminated catalyst can be removed from the transfer channel 54 via the discharge nozzle 64 and taken to regeneration. When required, a portion of the contaminated catalyst may be returned via an opening 56 controlled by valve 55 back to the reactor. While the return opening 56 is not essential to the function of the reactor, in some cases a partial return of contaminated catalyst to the reactor may promote the reaction. In the transfer channel 54, the contaminated catalyst moves downward in a dense phase, whereby communicating between the gas flows of the reactor and the regenerator via the catalyst transfer channel 54 is prevented. Gases are removed from the reactor cyclone via the cyclone center tube 57 and the nozzle 45. The catalyst flow entering the reactor from the regenerator via the nozzle 47 passes along the return channel 60. If the catalyst flow is in fluidized state, the gas carried over is separated from the catalyst in the catalyst return chamber 61. The catalyst flow into the reactor via the opening 62 is controlled by means of the valve 58. The valve 58 having a cylindrical control element is mechanically moved via bars 59 connected thereto. In some applications, the mechanical valves can be replaced by pneumatic valves.

The following are examples of conditions under which the reactor according to the invention can be used:

EXAMPLE III CATALYTIC CRACKING

| | |
|---|---|
| Reaction | Endothermic |
| Process temperature | 520–650° C. |
| Reaction time | 0.5–5 s |
| Catalyst | Conventional or latest FCC catalysts |
| Feed | Light gas oil, heavy gas oil, light bottom oils |
| Products | Light olefins, gasoline |

EXAMPLE IV THERMAL CRACKING

| | |
|---|---|
| Reaction | Endothermic |
| Process temperature | 650–950° C. |
| Reaction time | 0.2–0.5 s |
| Solids | Inert particulate matter, possibly with catalytic properties |
| Feed | Bottom oils, other heavy hydrocarbon-containing feeds with a substantial content of volatile fractions |
| Products | Light olefins, gasoline, gas oils |

EXAMPLE V DEHYDRATION

| | |
|---|---|
| Reaction | Endothermic |
| Process temperature | 600–750° C. (about 650° C. for $C_4$, about 700° C. for $C_3$, about 750° C. for $C_2$) |
| Reaction time | 0.4–2 s |
| Solids | Dehydrogenation catalyst: type Cr—$Al_2O_3$, V—Ca or V—Zr |
| Feed | Isobutane, n-butane, propane, ethane |
| Products | Isobutene, butenes, propene, ethene |

EXAMPLE VI OXIDATIVE DIMERIZATION OF METHANE

| | |
|---|---|
| Reaction | Exothermic |
| Process temperature | 800–900° C. |
| Reaction time | 0.08–0.3 s |
| Solids | Zr—La—Sr, $La_2O_3$—CaO |
| Feed | Natural gas, oxygen |
| Products | Ethene |

EXAMPLE VII GASIFICATION

| | |
|---|---|
| Reaction | Exothermic or autothermic |
| Process temperature | 1000–1300° C. (thermal partial oxidation) 700–1000° C. (catalytic partial oxidation) |
| Pressure | 10–40 bar (thermal partial oxidation) 1–10 bar (catalytic partial oxidation) |
| Feed | Hydrocarbon-containing material, e.g., natural gas, coal, bottom oil and/or biomass |
| Products | Hydrogen and carbon-monoxide-containing synthesis gas |

What is claimed is:

1. A method of converting hydrocarbons comprising:

step a) passing a gaseous or liquid feed into a circulating fluidized-bed reactor having a reaction space wherein particulate matter is in the fluidized state;

step b) converting the feed at a temperature of 100–1300° C.; and step c) removing the converted hydrocarbon products wherein said circulating fluidized-bed reactor (1–3; 41–43) has an axially annular cross section and is equipped with a multi-inlet cyclone (14, 17; 52, 63) disposed along an upper end, and inside, of the reactor for the separation of the particulate matter from the converted hydrocarbon products.

2. The method as defined in claim 1, wherein the reaction space comprises an intershell riser space (13; 50) formed between two concentrically located cylindrical and/or conical envelope surfaces.

3. The method as defined in claim 1 or 2, wherein the residence time of said hydrocarbon feed is 0.05–10 s.

4. The method as defined in claim 1 wherein said multi-inlet cyclone is equipped with louvered vanes (14; 63).

5. The method as defined in claim 1, wherein the particulate matter is a cracking catalyst and the converting step (b) is a catalytic cracking of a feed containing light gas oil, heavy gas oil and/or light bottom oil, at a process temperature of 520–650° C. using 0.5–5 s residence time, for preparing light olefins with the concurrent contamination of the catalyst.

6. The method as defined in claim 5, wherein the contaminated catalyst is transferred from the reactor to a regenerator for regeneration and then returned from the regenerator back to the reactor after the regeneration step.

7. The method as defined in claim 6, wherein the contaminated catalyst is regenerated in another circulating fluidized-bed reactor of axially annular cross section and being adapted concentric with the reactor used for converting the hydrocarbon feed.

8. The method as defined in claim 1, wherein thermal cracking is performed at a process temperature of 650–950° C., using 0.2–0.5 s residence time, for the purpose of preparing hydrocarbons which are lighter than the hydrocarbon feed.

9. The method as defined in claim 1, wherein dehydrogenation is performed on a feed containing pentanes, isobutane, n-butane, propane and/or ethane at a process temperature of 500–750° C., using 0.4–2 s residence time, for the purpose of preparing amylenes, isobutene, butenes, propene or ethene, respectively.

10. The method as defined in claim 1, wherein oxidation of natural gas with oxygen is performed at a process temperature of 800–900° C., using 0.08–0.3 s residence time, for the purpose of dimerizing methane.

11. The method as defined in claim 1, wherein thermal or catalytic gasification is performed on a hydrocarbon-containing feed at a process temperature of 700–1300° C. for the purpose of preparing synthesis gas.

12. The method as defined in claim 5, wherein the light olefins are propene, butenes, or amylenes and/or gasoline.

* * * * *